United States Patent [19]

Maki et al.

[11] Patent Number: 4,556,751

[45] Date of Patent: Dec. 3, 1985

[54] CATALYTIC ISOMERIZATION PROCESS OF DIMETHYLNAPHTHALENES

[75] Inventors: Takao Maki, Fujisawa; Tetsuo Masuyama, Machida; Yoshio Asahi, Sagamihara, all of Japan

[73] Assignee: Mitsubishi Chemical Industries Limited, Tokyo, Japan

[21] Appl. No.: 579,958

[22] Filed: Feb. 14, 1984

[51] Int. Cl.$^4$ .............................. C07C 5/22; C07C 5/30
[52] U.S. Cl. .................................................... 585/481
[58] Field of Search ....................................... 585/481

[56] References Cited

U.S. PATENT DOCUMENTS

| | | | |
|---|---|---|---|
| 3,780,119 | 12/1973 | Shimada et al. | 585/481 |
| 3,803,253 | 4/1974 | Said et al. | 585/481 |
| 3,806,552 | 4/1974 | Oka et al. | 585/481 |
| 3,855,328 | 12/1974 | Hedge | 585/481 |
| 3,888,938 | 6/1975 | Ogasawara et al. | 585/481 |
| 3,957,896 | 5/1976 | Yokoyama et al. | 585/481 |
| 4,041,089 | 8/1977 | Allen et al. | 585/481 |

*Primary Examiner*—D. E. Gantz
*Assistant Examiner*—A. Pal
*Attorney, Agent, or Firm*—Oblon, Fisher, Spivak, McClelland & Maier

[57] ABSTRACT

Catalytic isomerization of 10 types of dimethylnaphthalenes, which are classified into four groups, can be carried out by using as a catalyst a zeolite defining the main pore opening consists of a ten-membered oxygen ring.

8 Claims, 1 Drawing Figure

CATALYTIC ISOMERIZATION PROCESS OF DIMETHYLNAPHTHALENES

BACKGROUND OF THE INVENTION

(1) Field of the Invention

This invention relates to a catalytic isomerization process of dimethylnaphthalene. Particularly, this invention relates to a catalytic isomerization process suitable for producing the 2,6-isomer from a mixture of dimethylnaphthalene isomers.

(2) Description of the Prior Art

Dimethylnaphthalene consists of 10 isomers, which can be classified into the following four groups. Their isomerization can be readily carried out within their respective groups but is difficult to achieve between their respective groups.

(1) 1,5-, 1,6- and 2,6-isomers;
(2) 1,8-, 1,7- and 2,7-isomers;
(3) 1,4-, 1,3- and 2,3-isomers; and
(4) 1,2-isomer.

A principal end use of dimethylnaphthalene is the production of naphthalenedicarboxylic acid. For this application, the 2,6-isomer has found particularly preferred utility. On the other hand, the dimethlynaphthalene fraction separated from the recycled oil of the FCC process, whose fraction is the one of industrial supply sources of dimethylnaphthalene, or from coal tar fraction, is a mixture of ten isomers. In order to obtain the 2,6-isomer in a large volume, it is thus necessary to isomerize the other isomers into the 2,6-isomer. Many examples have been known with respect to isomerization of the above isomer within their respective groups, but isomerization between their respective groups has scarecely been known. For example, it has been proposed to perform the isomerization of dimethylnaphthalene by using mordenite, which is a sort of zeolite, as a catalyst (see, Japanese Patent Publication No. 47,020/1980). However, the above catalyst is unsuitable for isomerization between the groups.

SUMMARY OF THE INVENTION

An object of this invention is to provide a catalytic isomerization process of dimethylnaphthalenes, which process is adapted to produce with ease 2,6-dimethylnaphthalene from other dimethylnaphthalene isomers particularly from 1,8-, 1,7-, 2,7-, 1,4-, 1,3-, 2,3- and 1,2- other than the 1,5-, 1,6-dimethylnaphthalene isomers. The above object has been achieved by catalytically isomerizing dimethylnaphthalenes in the presence of a catalyst, i.e., a zeolite defining main interstices the inlets of which consists of a ten membered oxygen ring.

DETAILED DESCRIPTION OF THE INVENTION

Figure 1:
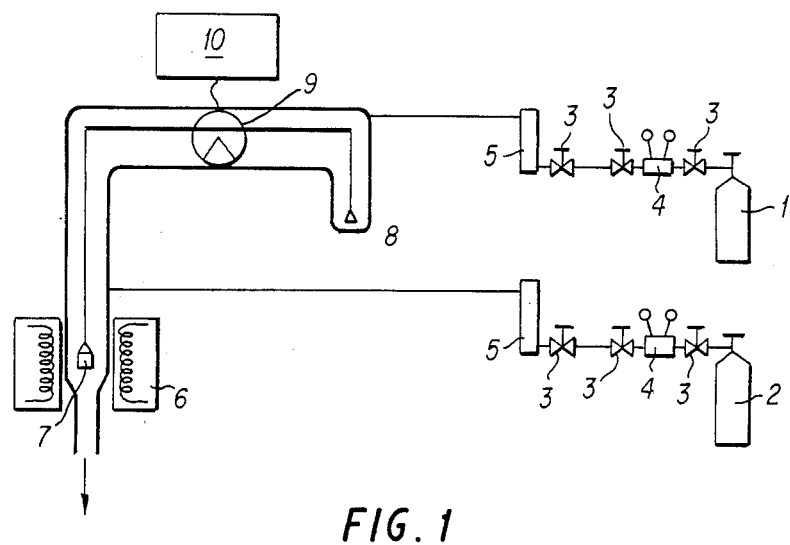
FIG. 1 is a schematic flow chart of a measurement instrument which was used to determine the acid amount of aluminosilicate by means of the gaseous base adsorption method. In the drawing: 1 . . . helium gas cylinder, 2 . . . standard ammonia gas cylinder, 3 . . . needle valves, 4 . . . reducing valves, 5 . . . rotameters, 6 . . . heating furnace, 7 . . . specimen, 8 . . . balancing weight, 9 . . . control system and 10 . . . recorder.

The invention will hereinafter be described in detail. As dimethylnaphthalene which may be used as a raw material for isomerization in accordance with the process of this invention, may be employed synthetic dimethylnaphthalene obtained by methylating naphthalene or methylnaphthalene or a dimethylnaphthalene fraction separated by distillation from a cracked oil which has been obtained by cracking petroleum fractions by various methods. The above-mentioned dimethylnaphthalene fraction separated by distillation from the recycled oil in the FCC process may be suitably used. The dimethylnaphthalene fraction obtainable from coal tar fraction is another suitable source. The residue, which occurs after separating one or more desired dimethylnaphthalene isomers from the isomerized mixture of each dimethylnaphthalene fraction, may also be used as a raw material for the process of this invention. Since each catalyst useful in the practice of the process of this invention has sufficient isomerizing capacity between the above-mentioned groups, the present invention may be advantageously applied for the isomerization of dimethylnaphthalene in which the proportion of the group, to which the 2,6-isomer belongs, has not reached the level in a composition equilibrated thermodynamically under isomerizing reaction conditions. Among various dimethylnaphthalene isomer compositions, the present invention can be most advantageously applied to dimethylnaphthalene in which the proportion of the group of the 1,8-, 1,7- and 2,7-isomers is higher than its level in thermodynamically-equilibrated level.

The catalyst useful in the practice of this invention is a zeolite defining the main pore opening consists of a ten-membered oxygen ring, for example, aluminosilicate or crystalline iron silicate. Such aluminosilicate has been known. Typical examples of such aluminosilicate are ZSM-5, 8, 11, etc. announced by Mobil Oil Corporation. Aluminosilicate of the above type generally has the pentasil structure and its silica/alumina molar ratio is normally 12 or higher. Generally speaking, the framework structure of aluminosilicate consists of silica and alumina but Fe, Cr and other metals may make up parts of the framework structure. In other words, aluminosilicate may contain some metals as non-exchangeable metals. On the other hand, crystalline iron silicate has also been known. As one representative example of such crystalline iron silicate, may be mentioned HCS announced by shell. Generally, crystalline iron silicate of this type has the pentasil structure and its $SiO_2$/$Fe_2O_3$ molar ratio is normally 12 or higher. There are also known some other types of crystalline iron silicates in each of which parts of its framework structure are substituted by metals other than Si and Fe, for example, by Al, B, Ga, etc.

In the process of this invention, these zeolites are used as acid-types for the reaction. As is well-known, the term "acid-type zeolite" means that the zeolite contains, as cations, protons and multivalent cations such as rare earth ions. Zeolites are normally applied for reactions as hydrogen-type zeolites. The zeolite may be employed in neat form or may be employed after it has been pelletted together with an additive such as silica, alumina, silica-alumina or kaolin, etc.

The aluminosilicate, which is used as a catalyst in the process of this invention and defines the main pore opening consists of a ten-membered oxygen ring, has different acid contents depending on its production conditions. According to an investigation carried out by the present inventors, it has been found that there is a correlation between an acid amount determined at 300° C. by the below-described gaseous base adsorption method and isomerizing capacity between groups of isomers. The isomerizing capacity between groups generally increases as the acid amount becomes higher. In order to conduct isomerization on an industrial scale between groups of isomers, it is advantageous to use aluminosilicate having an acid amount of 0.1 mmol/g or higher, preferably 0.45 mmol/g or higher.

The isomerization of dimethylnaphthalenes in accordance with the process of this invention may be carried out in both vapor and liquid phases. Vaporphase isomerization will hereinafter be described. The reaction is effected using a fixed-bed reactor, but may also be carried out using a fluidized-bed reactor, moving-bed reactor or the like. The reaction temperature may range from 100° to 550° C., preferably from 250° to 450° C., and more preferably from 300° to 450° C. The reaction pressure may range from 0.1 to 100 atoms with the range of from normal pressure to 20 atoms being preferred. Neat dimethylnaphthalene vapor may be brought into contact with the catalyst. Alternatively, it may be brought into contact with the catalyst after diluted with hydrogen, nitrogen, carbon dioxide or steam. The total gaseous space velocity may be 100–10,000 hr$^{-1}$, and preferably 500–5,000 hr$^{-1}$ under standard conditions (NTP). The liquid weight hourly space velocity (WHSV) of dimethylnaphthalene may usually be 0.01–100 ml/g-cat.hr, or preferably 0.1–10 ml/g-cat.hr.

Then, the liquid phase isomerization will be described. The reaction is carried out using normally a suspended-bed or fixed-bed reactor. The reaction temperature may generally range from 250° to 550° C., preferably from 250° to 450° C., and more preferably from 300° to 450° C. The pressure may generally range from normal pressure to 50 atoms. Excessive pressure is not essential so long as the pressure is high enough to maintain dimethylnaphthalene in a liquid state. Thus, the pressure is determined from economical or technical consideration. In the case of a suspended-bed reactor, the reaction may be carried out by batch or flow systems. The proportion of the catalyst to be charged may generally be 0.5–50 wt. %, and preferably 1–20 wt. %, both based on the raw material. The reaction is completed in about 0.1–10 hours. In the case of a fixed-bed reactor, the liquid hourly space velocity (LHSV) of dimethylnaphthalene is selected suitably from the range of 0.1–100 hr$^{-1}$. Dimethylnaphthalene may be brought into contact with the catalyst, either in neat state or in an atmosphere of hydrogen, nitrogen or carbon dioxide.

In accordance with the process of this invention, the 2,6-isomer may be produced with ease from other isomers which have been difficult for conversion to the 2,6-isomer in prior art.

The present invention will hereinafter be described in further detail by the following Examples. It should however be borne in mind that the present invention will not be limited to the following Example so long as it does not depart from its gist.

By the way, acid contents which are to be determined at 300° C. by the gaseous adsorption method in this invention are to be measured in accordance with the following method.
(i) Instrument: A TGA-type thermal analyzer (manufactured by Shimadzu Seisakusho Ltd.) equipped with a inlet for standard ammonia gas (see, FIG. 1).
(ii) Operation:
  (a) The apparatus is purged by helium gas at normal pressure of a flow velocity of 50 ml/min. The stream of helium gas is maintained until the measurement is finished.
  (b) A specimen is charged in the apparatus.
  (c) The internal temperature of the apparatus is raised up to 500 ° C. and is held for 2 hours at that temperature. The weight ($W_1$ g) of the specimen is then measured.
  (d) Standard ammonia gas (hilium gas containing 10% by volume of ammonia) is started to flow at 50 ml/min. into the apparatus. The weight of the specimen begins to increase as ammonia is adsorbed on the specimen.
  (e) Upon confirming that the weight of the specimen has reached constant, the internal temperature of the apparatus is lowered to 300° C. and the interior of the apparatus is thereafter held at 300° C. until the measurement is completed.
  (f) Upon confirming the specimen has reached another constant weight, the supply of the standard ammonia gas is stopped. Ammonia adsorbed on the specimen starts desorbing, thereby causing the weight of the specimen to begin to drop.
  (G) When the weight of the specimen has reached a further constant value, the weight ($W_2$ g) is measured.

$$\text{Acid content at } 300° \text{ C.} = \frac{(W_2 - W_1) \times 1000}{17 \times W_1} \text{ (mmol/g)}$$

Conversions and selectivities, which will be given in the following Examples, were calculated in accordance with the following equations, on the basis of the following components detected by gas chromatography.
Determined components: naphthalene, α- and β-methylnaphthalenes, α- and β-ethylnaphthalenes, all dimethylnaphthalene isomers.

$$\text{Conversion (\%)} = \frac{\text{Total components (mol) detected by gas chromatography} - \text{recovered raw material (mol)}}{\text{Total components (mol) detected by gas chromatography}} \times 100$$

$$\text{Selectivity (\%)} = \frac{\text{Each component (mol) detected}}{\text{Total components (mol) detected by gas chromatography} - \text{recovered raw material (mol)}} \times 100$$

EXAMPLE 1

(i) Synthesis of aluminosilicate

Charged into a stainless steel autoclave having an internal volume of 100 liters were 32.471 Kg of colloidal silica (silica content: 20.4 wt. %), 18.8 Kg of water and 7.228 Kg of diglycolamine. The contents were agitated, followed by an addition of a solution which had been obtained by dissolving 499.3 g of sodium aluminate (purity: 90.3 wt. %) and 726 g of sodium hydroxide in 10 Kg of water. After sealing the autoclave, the contents were heated with stirring at 160° C. for 3 days. The thus-obtained product was washed with about 100 Kg of water and then dried at 130° C. It was confirmed that the resulting product had a silica/alumina ratio of 27, its diffraction pattern obtained by the powder X-ray diffraction analysis was similar to that disclosed in Example 1 of Japanese Patent Laid-open No. 92,114/1981 and thus it was a pentasil aluminosilicate defining the main pore opening consists of a ten-membered oxygen ring.

(ii) Conversion to acid type aluminosilicate

Thirty six grams of the above-obtained aluminosilicate were charged in an aqueous solution containing 53.3 g of ammonium chloride dissolved in 200 ml of water. The resultant mixture was refluxed for 2 hours. After collecting the thus-treated aluminosilicate by filtration, it was subjected twice to a similar refluxing treatment. The thus-treated aluminosilicate was washed with deionized water until no chlorine ions were detected (the detection of chlorine ions was carried out by an 0.1-N aqueous solution of silver nitrate). The resulting product was then dried at 130° C. and pelletted by a tableting machine. Thereafter, the thus-formed tablets were ground and shieved to 24-42 mesh. The resultant granule was calcined at 500° C. for 3 hours in the stream of air, thereby obtaining acid-type aluminosilicate.

(iii) Isomerizing reaction

Packed in a reactor having an internal diameter of 10 mm and made of a heat-resistant glass was 1.5 ml of the above-obtained acid-type aluminosilicate. The reactor was placed in an electric furnace and heated to 350° C. A 10 wt. % solution of 2.6-dimethylnaphthalene diluted in benzene and hydrogen were introduced at normal pressure into the reactor, respectively at flow velocities of 3.12 ml/hr and 1 liter/hr (NTP) so that an isomerizing reaction was proceeded. Gaseous effluent, which flew out of the reactor, was collected in a cold trap. Liquid reaction product, which was collected for 1 hours after the initiation of the reaction, was analyzed by gas chromatography. Results are shown in Table 1. Incidentally, carbon deposit was hardly observed on the aluminosilicate.

EXAMPLE 2

To a beaker made of heat-resistant glass, 22.9 g of silica gel (product of Fuji-Davison Chemical Limited "Special Silicagel Grade 923") and 120 ml of a 2.36-N aqueous solution of tetrapropylammonium hydroxide [$(CH_3CH_2CH_2)_4NOH$]. The contents were heated to 80° C., followed by an addition of a solution which had been obtained by dissolving 2.384 g of sodium aluminate (purity : 90 wt. %) in 63 ml of water. The beaker was placed in an autoclave having an internal volume of 1 liter. After sealing the autoclave, the contents were heated at 150° C. for 6 days. The resultant product was collectd by filtration and washed with 1 liter of deionized water. The thus-washed product was then dried at 130° C. for 2 days. It was confirmed that the thus-obtained product had a silica/alumina ration of 19, its diffraction pattern obtained by powder X-ray diffraction was similar to that disclosed in Example 1 of Japanese Patent Publication No. 10.064/1971 and it was "ZMS-5" zeolite defining the main pore opening consists of a ten-membered oxygen ring. Similar to Example 1, the zeolite was converted to the acid-type zeolite, whereby conducting the isomerization of 2,6-dimethylnaphthalene. Results are summarized in Table 1.

EXAMPLE 3

Charged into a beaker made of heat-resistant glass were 108 g of water glass (JIS Grade-3 product), 21.04 g of octamethylene diamine, 3.723 g of aluminum sulfate [$Al_2(SO_4)_3 \cdot 18H_2O$] and 292.32 g of water. The beaker was placed in an autoclave having an internal volume of 1 liter. The autoclave was then sealed and heated at 160° C. for 3 days. After washing the resulting product with one liter of deionized water, the thus-washed product was dried at 130° C. for 2 days.

It was confirmed that the thus-obtained product has a silica/alumina ratio of 37, its diffraction pattern obtained by powder X-ray diffraction was substantially the same as the pattern disclosed in Example 1 of Japanese Patent Publication No. 23,280/1978, and it was "ZSM-11" zeolite defining the main pore opening consists of a ten-membered oxygen ring.

Following the procedures of Example 1, the above zeolite was converted to the acid-type zeolite, whereby conducting the isomerization of 2,6-dimethylnaphthalene. Results are given in Table 1. Incidentally, carbon deposit was scarecely observed on the zeolite after completion of the reaction.

EXAMPLE 4

Charged into a beaker made of heat-resistant glass were 218 g of colloidal silica (silica content: 20 wt. %), 137.5 g of water and 31.8 g of diglycolamine. The contents were agitated, followed by an addition of a solution which had been prepared by dissolving 1.89 g of sodium aluminate (purity: 90 wt. %) and 6.82 g of sodium hydroxide in 50 g of water. The resulting mixture was stirred for 30 minutes. The thus-obtained gel-like mixture having a silica/alumina ratio of 70 was placed in an autoclave having an internal volume of one liter inserted a beaker. The autoclave was sealed and heated at 160° C. for 3 days. The resulting product was washed with 1 liter of deionized water and then dried at 130° C. for 2 days.

It was confirmed that the thus-obtained product had a silica/alumina ratio of 40, its diffraction pattern obtained by powder X-ray diffraction was similar to that disclosed in Example 1 of Japanese Patent Laid-open No. 92,114/1981 and it was a pentasil zeolite defining main pore opening consists of a ten-membered oxygen ring.

Similar to Example 1, the above-prepared zeolite was converted to the acid-type zeolite, whereby carrying out the isomerization of 2,6-dimethylnaphthalene. Results are shown in Table 1.

EXAMPLE 5

One hundred grams of 2,6-dimethylnaphthalene and 7.0 g of aluminosilicate prepared in accordance with the procedure of Example 1 were charged into an magnetically driven autoclave having an internal volume of 1 liter and made of SUS 316. The autoclave was sealed and its internal atmosphere was purged with nitrogen gas, thereby introducing 10 kg/cm$^2$G of nitrogen. The autoclave was then heated in an electric furnace to 350° C. in about 1 hour. After reaching 350° C., the stirring was initiated and the reaction was allowed to proceed for 2 hours. The gauge pressure was 22 kg/cm$^2$ and the revolution speed of the stirrer was 700 rpm. After the reaction, the autoclave was promptly cooled to bring its internal pressure to normal pressure. Then, the autoclave was opened and its contents were diluted with 500 ml of toluene. Thereafter, a portion of the thus-diluted reaction mixture was taken out of the autoclave and was analyzed by gas chromatography. Results are given in Table 1.

EXAMPLE 6

An isomerizing reaction was carried out in the same manner as in Example 5 except that the reaction temperature was changed to 320° C. Results are shown in Table 1.

EXAMPLE 7

An isomerizing reaction was conducted in the same manner as in Example 5 except that the zeolite prepared in Example 3 was employed. Results are given in Table 1.

COMPARATIVE EXAMPLE 1

Following the procedure of Example 1 except that synthetic mordenite (trade name: "Zeolon 100H"; product of Norton Company) was used, the isomerization of dimethylnaphthalene was carried out. Results are shown in Table 1. Incidentally, a large amount of carbon deposit was observed on the zeolite after completion of the reaction.

COMPARATIVE EXAMPLE 2

The synthetic mordenite of Comparative Example 1 was charged in a 6-N aqueous solution of hydrochloric acid and then heated and refluxed for 6 hours. After cooling the reaction mixture, the thus-treated mordenite was collected by filtration, washed with water until no chlorine ions were detected, and then dried at 130° C. The thus-dried product was pelletted by a tableting machine. Resultant tablets were graded and shieved to 24–42 mesh. The resulting granule was calcined at 500° C. for 3 hours in the stream of air, thereby obtaining a catalyst.

Using the above-obtained catalyst, the isomerization of dimethylnaphthalene was carried out in the same manner as in Example 1. Results are summarized in Table 1. A large amount of carbon deposit was observed on the mordenite after completion of the reaction.

EXAMPLE 8

(i) Synthesis of crystalline iron silicate

Charged into a round-bottomed, cylindrical vessel having an internal volume of 1 liter and made of glass were 143.2 ml of an aqueous solution containing 31.4 g of tetrapropylammonium and 30 g of powdery silica. The contents were agitated thoroughly, followed by an addition of a homogeneous solution containing 1.06 g of sodium nitrate and 6.94 g of iron nitrate dissolved in 30 ml of water. The resultant mixture was stirred thoroughly. The glass-made vessel containing the above materials was placed in an autoclave made of SUS 316. After sealing the autoclave, the contents were heated with stirring at 150° C. for 48 hours. The resulting product was cooled, washed with about 3 liters of water, and then dried at 130° C. for 24 hours. The thus-obtained product had an Si/Fe molar ratio of 41.8. Its diffraction pattern obtained by the powder X-ray diffraction analysis is shown in Table 2.

(ii) Conversion to acid-type

The above-obtained crystalline product was calcined at 500° C. for 3 hours in the stream of air. The thus-obtained product was charged in a 1-N aqueous solution of ammonium nitrate and refluxed for 2 hours. After collecting the thus-treated product by filtration, the same refluxing operation was repeated once. The resulting product was collected by filtration and washed with about 3 liters of deionized water. Thereafter, the thus-washed product was dried at 60° C. for 12 hours and then calcined at 500° C. for 3 hours in the stream of air to acid-type crystalline iron silicate.

(iii) Isomerizing reaction

The thus-prepared acid-type crystalline iron silicate was pelletted by a tableting machine. Resultant tablets were ground and shieved to 24–42 mesh. A 1.5 ml portion of the thus-prepared granule was packed in a reactor having an internal diameter of 10 mm and made of heat-resistant glass. The reactor was then placed in an electric furnace and heated to 400° C. After reaching

TABLE 1

| | Zeolite | | Reaction conditions | | | Reaction results Selectivity (%) | | | | |
|---|---|---|---|---|---|---|---|---|---|---|
| | Silica/alumina (molar ratio) | Acid content (mmol/g) | Pressure | (kg/cm².G) | Temp. (°C.) | Conversion (%) | NL + MN* | 1,6 + 1,5** | 1,7 + 1,8 + 2,7*** | (1,7+1,8+2,7) / (NL+MN) |
| Ex. 1 | 27 | 0.53 | Vapor phase | Normal pressure | 350 | 65.3 | 10.1 | 64.2 | 24.5 | 2.43 |
| Ex. 2 | 19 | 0.15 | Vapor phase | Normal pressure | 350 | 34.4 | 3.6 | 89.1 | 6.8 | 1.89 |
| Ex. 3 | 37 | 0.50 | Vapor phase | Normal pressure | 350 | 38.3 | 11.7 | 71.4 | 16.5 | 1.41 |
| Ex. 4 | 40 | 0.38 | Vapor phase | Normal pressure | 350 | 17.8 | 12.4 | 71.4 | 16.3 | 1.31 |
| Ex. 5 | 27 | 0.53 | Liquid phase | 22 | 350 | 71.6 | 4.5 | 62.9 | 26.1 | 5.8 |
| Ex. 6 | 27 | 0.53 | Liquid phase | 22 | 320 | 60.0 | 1.5 | 83.5 | 12.4 | 8.3 |
| Ex. 7 | 27 | 0.50 | Liquid phase | 22 | 350 | 51.6 | 1.2 | 90.8 | 7.7 | 6.4 |
| Comp. Ex. 1 | 10 | 1.26 | Vapor phase | Normal pressure | 350 | 68.9 | 32.4 | 54.7 | 11.1 | 0.34 |
| Comp. Ex. 2 | 102 | — | Vapor phase | Normal pressure | 350 | 85.8 | 63.4 | 26.3 | 7.1 | 0.11 |

*NL: naphthalene
MN: α- and β-methylnaphthalenes
**1,6 + 1,5: the sum of the 1,6-isomer and 1,5-isomer
***1,7 + 1,8 + 2,7: the sum of the 1,7-isomer, 1,8-isomer and 2,7-isomer 400° C., the reactor was purged for 1 hour by $N_2$ gas of flow rate at 1 liter/hr (NTP). Then, the stream of $N_2$ gas was switched to $H_2$ gas, which was charged at a flow rate of 1 liter/hr (NTP). At the same time, a 10 wt. % solution of 2,6-dimethylnaphthalene dissolved in benzene was introduced at 3.12 ml/hr, thereby carrying out the isomerizing reaction under normal pressure.

The reaction product from the reactor, was liquefied and collected in a cold trap. A portion of the liquid reaction product, which was been collected in 30 minutes after the initiation of the reaction, was taken out and analyzed by gas chromatography. Results are shown in Table 3. Then, the reaction temperature was raised to 450° C. and a liquid reaction product was collected for 30 minutes in the same manner. It was analyzed by gas chromatography. Results are shown in Table 3.

EXAMPLE 9

Using the catalyst obtained in Example 8, an isomerizing reaction was carried out under elevated pressure. Packed in a reactor made of SUS 316 and having an internal diameter of 19 mm was 3.6 ml (1.9 g) of the catalyst which had been shieved to 10–20 mesh. Molten 2,6-dimethylnaphthalene (2,6-DMN) and $H_2$ gas were introduced at a reaction temperature of 350° C. and a reaction pressure of 10 kg/cm$^2$·G. [Flow velocity of 2,6-DMN: 9 ml/hr; $H_2$/2,6-DMN = 12.5/1 (mol)].

A liquid reaction product was collected from the 90th minute to 120th minute after the initiation of the reaction. Thereafter, the temperature was raised without stopping the reaction. The reaction was thus carried out at 400° C. A liquid reaction product was collected from 30 minutes after the temperature reached 400° C. Portions of the liquid reaction products, which were obtained respectively at 350° C. and 400° C., were analyzed by gas chromatography. Results are given in Table 3.

EXAMPLE 10

Using the powdery catalyst prepared in Example 8, a liquid phase isomerizing reaction was carried out. One hundred grams of 2,6-DMN and 7.0 g of the catalyst were charged into a magnetically driven autoclave having an internal volume of 1 liter and made of SUS 316. After sealing the autoclave, the internal atmosphere was purged by nitrogen gas, thereby introducing 10 kg/cm$^2$·G of nitrogen. The autoclave was then heated to 400° C. in an electric furnace, at which temperature the reaction was conducted for 2 hours with stirring. The gauge pressure was 28 kg/cm$^2$ and the revolution speed of the stirrer was 700 rpm. After the reaction, the autoclave was cooled prompty. The thus-obtained liquid reaction product was diluted with 500 ml of toluene. A portion of the thus-diluted product was taken out of the autoclave and analyzed by gas chromatography. Results are shown in Table 3.

TABLE 2

| $2\theta$ | Relative intensity ($I/I_o$) | $2\theta$ | Relative intensity ($I/I_o$) |
|---|---|---|---|
| 8.05 | 72 | 23.30 | 100 |
| 8.95 | 46 | 23.90 | 36 |
| 11.95 | 3 | 24.05 | 50 |
| 13.30 | 8 | 24.55 | 32 |
| 14.05 | 14 | 26.05 | 12 |
| 14.90 | 20 | 27.15 | 11 |
| 15.60 | 11 | 29.40 | 11 |
| 16.05 | 14 | 30.05 | 15 |
| 16.65 | 4 | 30.45 | 8 |
| 17.80 | 8 | 31.35 | 3 |
| 19.35 | 6 | 32.90 | 5 |
| 20.45 | 9 | 34.50 | 5 |
| 20.95 | 13 | 36.10 | 6 |
| 21.80 | 3 | 37.60 | 4 |
| 22.30 | 7 | 45.20 | 8 |
|  |  | 45.60 | 9 |

TABLE 3

| | Zeolite Si/Fe (molar ratio) | Reaction conditions | | | | Reaction results | | | | | |
| | | | Pressure (kg/cm$^2$·G) | Temp. (°C.) | Conversion (%) | NL + MN* | Selectivity (%) | | | | $\dfrac{(1,7\text{-} + 1,8\text{-} + 2,7\text{-})}{NL + MN}$ |
| | | | | | | | 1,6- + 1,5-** | 1,7- + 1,8- + 2,7-*** | High b.p. | | |
| Ex. 8 | 41.8 | Vapor phase | Normal pressure | 400 | 56.2 | 1.2 | 95.2 | 3.6 | trace | | 3.0 |
| | | | | 450 | 60.4 | 3.8 | 86.4 | 8.8 | 0.9 | | 2.3 |
| Ex. 9 | 41.8 | Vapor phase | 10 | 350 | 29.4 | 1.0 | 88.5 | 10.1 | trace | | 10.1 |
| | | | | 400 | 41.5 | 1.5 | 82.0 | 15.8 | 0.4 | | 10.5 |
| Ex. 10 | 41.8 | Liquid phase | 28 | 400 | 57.7 | 2.4 | 87.1 | 7.9 | 1.4 | | 3.3 |

*NL: naphthalene
MN: the sum of α- and β-methylnaphthalenes
**the sum of 1,6-dimethylnaphthalene and 1,5-dimethylnaphthalene
***the sum of 1,7-dimethylnaphthalene, 1,8-dimethylnaphthalene and 2,7-dimethylnaphthalene As apparent from Tables 1 and 3, each zeolite defining the main pore opening consists of a ten-membered oxygen ring has excellent isomerizing capacity between groups of dimethylnaphthalene isomers rather than dimethylating activity. It is also readily envisaged that, among zeolites of the above type, an aluminosilicate having an acid content of 0.45 mmol/g or higher gave a high yield for isomers isomerized between isomer groups (yield = conversion × selectivity × 1/100) and is thus a particularly preferred catalyst.

EXAMPLES 11 and 12

Packed in a reactor having an internal diameter of 10 mm and made of heat-resistant glass was 1.5 ml of the acid-type zeolite prepared in Example 1. The reactor was placed in an electric furnace and heated to 350° C. A 5 wt. % solution of dimethylnaphthalene dissolved in benzene and hydrogen were introduced at normal pressure into the reactor, respectively at flow velocities of 3.12 ml/hr and 1 liter/hr (NTP), thereby conducting an isomerizing reaction. The reaction product from the reactor, was collected in a cold trap. A liquid reaction product collected in the course of 30 minutes from the beginning of the reaction was analyzed by gas chromatography. Results are given in Table 4.

TABLE 4

|     |                     | 2,7-isomer | 2,6-isomer | 1,7-isomer | 1,6-isomer |
|-----|---------------------|------------|------------|------------|------------|
| Ex. 11 | Raw material (%) | 95.4       | 2.7        |            | 1.3        |
|     | Liquid product (%)  | 39.8       | 6.7        | 38.0       | 7.0        |
| Ex. 12 | Raw material (%) | 0.8        | 99.2       |            |            |
|     | Liquid product (%)  | 8.1        | 37.7       | 6.3        | 35.9       |

EXAMPLES 13-15

Dry zeolite, which had been prepared in Example 1 and exchanged with ammonium ions, was pelletted by a tableting machine. Resultant tablets were ground and shieved to 10–14 mesh. The thus-obtained granule was calcined at 500° C. for 3 hours in air, thereby obtaining acid-type zeolite.

The above zeolite was packed in a reactor having an internal diameter of 25 mm and made of heat-resistant glass. The reactor was then placed in an electric furnace and heated to 350° C. Into the reactor, molten 2,6-dimethylnaphthalene and hydrogen were introduced at normal pressure, respectively at flow velocities of 0.848 g/hr and 1.8 liter/hr (NTP) to carry out an isomerizing reaction. The reaction product from the reactor, was collected by a cold trap. A liquid reaction product, which was collected in the course of 1 hour from the beginning of the reaction, was analyzed by gas chromatography. Results are given in Table 5.

TABLE 5

| Ex. | Catalyst volume (ml) | Conversion (%) | Selectivity (%) |  |  |  | 2,7 + 1,7 + 1,8 / NL + MN |
|-----|----------------------|----------------|-----------------|--|--|--|--|
|     |                      |                | NL + MN | 1,6 + 1,5 | 2,7 | 2,7 + 1,7 + 1,8 |  |
| 13  | 5                    | 76.7           | 9.9  | 35.7 | 21.9 | 48.0 | 4.8 |
| 14  | 2.5                  | 65.9           | 6.5  | 48.7 | 20.7 | 39.5 | 6.1 |
| 15  | 1.0                  | 41.3           | 5.8  | 54.4 | 25.8 | 36.4 | 6.3 |

EXAMPLE 16

Following the procedure of Example 5, an isomerizing reaction was carried out using the same catalyst as in Example 5 except that a mixture having the composition given in Table 6 was used as a reaction raw material. A portion of the liquid product obtained after completion of the reaction was analyzed by gas chromatography. Results are given in Table 6.

The reaction raw material was a fraction of the boiling point range of 257°–266° C. from recycled light oil obtained by the fluidized catalytic cracking of reduced-pressure light oil from petroleum refinery and then removing paraffins and 2,6-dimethylnaphthalene in accordance with the procedures described respectively in Examples of Japanese Patent Publication Nos. 16,963/1982 and 44,728/1972.

EXAMPLE 17

An isomerizing reaction was conducted using the same catalyst as in Example 8 and following the procedure of Example 8 except that the same mixture as that used in Example 16 was used as a reaction raw material. A liquid was collected for 30 minutes after the initiation of the reaction at 400° C. A portion of the liquid was analyzed by gas chromatography. Results are given in Table 6.

TABLE 6

| Ex. | Zeolite (molar ratio) |  |  | NL | MN | EN* | DMN |  |  |  |  |  | TMN** |
|-----|-----------------------|--|--|----|----|-----|-----|--|--|--|--|--|------|
|     |                       |  |  |    |    |     | 2,6 | 2,7 | 1,6 | 1,7 + 1,5 | 1,3 + 1,4 | 2,3 |  |
| 16  | Silica/alumina = 27   | Liquid phase | Raw material (wt. %) | 0.6 | 1.5 | 14.8 | 1.4 | 11.8 | 18.4 | 21.9 | 24.6 | 3.2 | 1.8 |
|     |                       |              | Liquid product (wt. %) | 7.1 | 4.0 | 4.9 | 11.4 | 12.5 | 11.7 | 15.0 | 20.3 | 6.1 | 3.9 |
| 17  | Si/Fe = 41.8          | Vapor phase  | Liquid product (wt. %) | 5.9 | 2.2 | 7.4 | 9.5 | 11.9 | 13.9 | 18.2 | 22.8 | 5.2 | 1.7 |

*EN: ethylnaphthalene
**TMN: trimethylnaphthalene

EXAMPLE 18

137.5 g of water and 31.8 g of diglycolamine were added to 218 g of colloidal silica (silica content: 20 wt. %). The resultant mixture was agitated, followed by an addition of a solution containing 1.89 g of sodium sluminate (purity: 90 wt. %) and 6.82 g sodium hydroxide dissolved in 50 g of water. The thus-obtained mixture was stirred for 30 minutes. The thus-obtained gel-like mixture the silica/alumina ratio of which had been adjusted to 70 was charged in an autoclave equipped with an inner cylinder having an internal volume of 1 liter and made of Pylex glass and was heated at 160° C. for 72 hours. The resulting reaction product was washed with 1 liter of dechlorinated water, collected by filtration, and then heated and dried at 130° C. The thus-obtained product had a silicon/alumina ratio of 39.8 and its X-ray diffraction pattern was the same as that disclosed in Example 1 of the aforementioned Japanese Patent Laid-open No. 92114/1981.

The thus-obtained zeolite was converted to H-type in accordance with the following procedure. Namely, 66 g of the above zeolite was charged in an aqueous solution containing 80.2 g of ammonium chloride dissolved in 300 ml of water. The resulting mixture was refluxed for 2 hours and, after collecting the thus-treated zeolite by filtration, a similar refluxing treatment was additionally repeated twice. The resulting zeolite was then washed with dechlorinated water until no chlorine ions were detected. The detection of chlorine ions was conducted with a 0.1 N solution of silver nitrate in water. Thereafter, the thus-treated zeolite was dried at 130° C. and, after molding it by a powder tableting machine, was ground and classified to 10–14 mesh. The resulting tures a high selectivity for 2,7-DMN from 2,6-DMN reduces substaintially and carbon deposit on catalyst.

TABLE 7

| Ex. | Reaction temp. (°C.) | Conversion (mol %) | Selectivity of each component produced (mol %) | | | | | Carbon balance (mol %)* | Carbon deposit |
|---|---|---|---|---|---|---|---|---|---|
| | | | NL + MN | 1,6 + 1,5 | 2,7 | 1,7 | 2,3 | | |
| Example 18 | 300 | 10.7 | 8.9 | 70.8 | 16.0 | — | — | 96.3 | little |
| | 350 | 24.4 | 6.9 | 50.5 | 34.7 | 3.7 | 2.3 | 100.3 | |
| | 400 | 41.1 | 6.3 | 57.4 | 27.5 | 6.1 | 1.4 | 96.2 | |
| | 450 | 61.7 | 8.2 | 57.6 | 21.7 | 10.8 | 0.9 | 68.9 | |
| | 500 | 73.2 | 10.4 | 50.0 | 21.4 | 14.7 | 0.9 | 87.1 | |
| Comp. Ex. 3 | 350 | 71.5 | 18.2 | 45.6 | 11.0 | 10.0 | 0.5 | 49.1 | Severe |
| | 500 | 70.1 | 16.7 | 54.0 | 7.7 | 8.0 | 0.3 | 85.1 | |

*Carbon balance (mol %):
$$\frac{\text{Total products detected by gas chromatography (mole)}}{\text{Charged 2,6-DMN (mole)}} \times 100$$

powder was heated and burnt at 500° C. for 3 hours in air to obtain an H-type reaction catalyst useful in the practice of this invention.

Then, 10 g of the above-obtained reaction catalyst was packed in a reactor having an internal diameter of 25 mm and made of heat-resistant glass. The reactor was placed in an electric furnace and heated to a predetermined temperature. Thereafter, molten 2,6-dimethyl-naphthalene, a raw material, and hydrogen were caused to flow respectively at flow velocities of 1.7 g/hr and 1.8 liters/hr (NTP) to the catalyst layer. Namely, 2,6-dimethylnaphthalene and hydrogen were caused to pass through the catalyst layer at each of the reaction temperatures of 300° C., 350° C., 400° C., 450° C. and 500° C. At each of the reaction temperature, the reaction was allowed to proceed for 30 minutes and the resulting liquid reaction product was collected by dissolving it in refluxed toluene. The reaction was not discontinued during each temperature-raising period. Each collected liquid was analyzed by gas chromatography. Results are summarized in Table 7. The gas chromatographic analysis of the product was carried out by using a glass capillary column containing 2% of Benton 34 and 2% of didecylphthalate and having an internal diameter of 0.25 mm and a length of 40 m.

COMPARATIVE EXAMPLE 3

An isomerizing reaction was carried out in the same manner as in Example 18 except that the catalyst was replaced by synthetic H-type mordenite (product of Norton Company; trade name: "Zeolon 100H") and the reaction temperature was changed to 350° C. and 500° C. For comparison, results are also summarized in Table 7.

From the results given in Table 7, it is understood that the process of this invention is far superior to the prior process, which uses the synthetic H-type mordenite catalyst. The process of the present invention fea-

EXAMPLE 19

Into a tubular reactor having an internal diameter of 19 mm and made of glass, 7.3 ml (4.2 g) of the acid-type aluminosilicate obtained in Example 1 was packed. Then, molten 2,3-DMN and N₂ gas were introduced at normal pressure and 350° C. At a flow rate of 1.33 g/hr and 2.8 liters/hr (NTP), respectively, through a preheater to a catalyst column by means of an "SUS-304" made injector the temperature of which was controlled at 120° C. The liquid reaction product was collected in refluxed toluene. The liquid reaction product was collected for 30 minutes after the initiation of the reaction. A portion of the liquid reaction product was analyzed by gas chromatography. Results are shown in Table 8.

EXAMPLE 20

A reaction was carried out in the same manner as in Example 19 except that the raw material was changed to 1,3-DMN. Results are given in Table 8.

COMPARATIVE EXAMPLE 4

A reaction was conducted in the same manner as in Example 19 except that the raw material was changed to 2,6-DMN. Results are shown in Table 8.

It is apparent from Examples 19 and 20 and Comparative Example 4 that the shifting rate of each methyl group to its adjacent ring in 2,3-DMN or 1,3-DMN, i.e., $[(DMN)_N]$ is faster by twice or more than the rate of each methyl group to another site of the same ring in 2,6-DMN, i.e., $[(DMN)_S]$.

TABLE 8

| Example or Comparative Example | Raw material | Yield (%) | | | | | | | | $(DMN)_S$ or $(DMN)_N$* |
|---|---|---|---|---|---|---|---|---|---|---|
| | | NL + MN | DMN | | | | | | TMN | |
| | | | 2,6 | 1,6 | 2,7 | 1,7 + 1,5 | 1,3 + 1,4 | 2,3 | | |
| Example 19 | 2,3-DMN | 7.5 | 5.4 | 4.7 | 4.4 | 4.7 | 52.8 | 16.7 | 3.7 | $(DMN)_N$ = 19.2 |
| Example 20 | 1,3-DMN | 6.3 | 5.0 | 4.1 | 4.1 | 4.7 | 50.7 | 17.0 | 4.4 | $(DMN)_N$ = 17.9 |
| Comparative Example 4 | 2,6-DMN | 8.7 | 18.4 | 20.6 | 17.1 | 19.3 | 6.4 | 2.6 | 6.8 | $(DMN)_S$ = 9.0 |

*$(DMN)_S$: 1,3-DMN + 1,4-DMN + 2,3-DMN
$(DMN)_N$: 2,6-DMN + 1,6-DMN + 2,7-DMN + 1,7-DMN + 1,5-DMN

What is claimed is:

1. A process for catalytically isomerizing dimethyl-naphthalene which comprises, using a zeolite having pore windows provided by ten-membered oxygen rings, said zeolite being (1) an acid-type pentasil aluminolsilicate having a silica/alumina molar ratio of 12 of higher and an acid content of 0.1 mmol/g or higher at 300° C. as determined by gaseous base absorption, or said zeolite being (2) an acid-type pentasil iron silicate having a $SiO_2/Fe_2O_3$ molar ratio of 12 or higher.

2. A process as claimed in claim 1, wherein the total content of 1,5-, 1,6- and 2,6-dimethyl-naphthalenes in the dimethylnaphthalene is lower than the thermodynamically-equilibrated level under isomerization conditions.

3. A process as claimed in claim 1, wherein the aluminosilicate has an acid content of 0.45 mmol/g or higher at 300° C. when determined by the gaseous base adsorption method.

4. The process of claim 1, wherein said dimethylnaphthalene being isomerized is at least one member selected from the group consisting of 1,8-dimethylnaphthalene, 1,7-dimethylnaphthalene, 2,7-dimethylnaphthalene, 1,4-dimethylnaphthalene, 1,3-dimethylnaphthalene, 2,3-dimethylnaphthalene and 1,2-dimethylnaphthalene.

5. The process of claim 4, wherein 2,6-dimethylnaphthalene is produced.

6. The process of claim 1, wherein said zeolite is at least one member selected from the group consisting of ZSM-5 zeolites, ZSM-8 zeolites, ZSM-11 zeolites and HCS zeolites.

7. The process of claim 1, wherein the isomerization is carried out at a temperature within the range of from about 100° to 550° C.

8. A process a catalytically isomerizing dimethylnaphthalene which comprises contacting said dimethylnaphthalene with a zeolite having pore windows provided by ten-membered rings containing oxygen.

* * * * *